(12) United States Patent
Sada

(10) Patent No.: US 10,575,524 B1
(45) Date of Patent: Mar. 3, 2020

(54) METHOD OF PROTECTING FIELD CORN FROM DAMAGE BY A PLANT PATHOGEN

(71) Applicant: SUMITOMO CHEMICAL COMPANY, LIMITED, Tokyo (JP)

(72) Inventor: Yoshinao Sada, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/396,506

(22) Filed: Apr. 26, 2019

(30) Foreign Application Priority Data

Mar. 29, 2019 (JP) .................. 2019-066003

(51) Int. Cl.
*A01N 43/653* (2006.01)

(52) U.S. Cl.
CPC .................. *A01N 43/653* (2013.01)

(58) Field of Classification Search
None
See application file for complete search history.

(56) References Cited

U.S. PATENT DOCUMENTS

2014/0155262 A1* 6/2014 Dietz .................. A01N 43/653
504/100

FOREIGN PATENT DOCUMENTS

WO   WO 2013/007767 A1   1/2013

OTHER PUBLICATIONS

Mefentrifluconazole Data Sheet at http://www.alanwood.net/pesticides/ mefentrifluconazole.html (retrieved from the internet Jul. 5, 2019) (Year: 2019).*
Bergstrom G.C. in Foliar Fungicides for Field Corn in New York at https://fieldcrops.cals.cornell.edu/sites/fieldcrops.cals.cornell.edu/files/shared/documents/CornFungicideBergstronn6.21.12%2520edit.connpressed.pdf (2001) (retrieved from the internet Jul. 5, 2019) (Year: 2001).*
Corn Disease Management at https://cropwatch.unl.edu /UNL-EC130-Corn-Disease-Trtmt-Tables.pdf (2016) (retrieved from the internet Jul. 5, 2019) (Year: 2016).*
Mefentrifluconazole General Information at http://web.archive.org/web/20170713075026/https://sitem. herts.ac.uk/aeru/ppdb/en/Reports/3098.htm (retrieved from the internet Jul. 5, 2019) (Year: 2017).*
"BestFoodFacts.org", https://www.bestfoodfacts.org/corn/, Apr. 26, 2019, total of 10 pages.
Echt et al., "Evidence for the Inclusion of Controlling Elements within the Structural Gene at the Waxy Locus in Maize,", Genetics 99: pp. 275-284, Oct. 1981.

* cited by examiner

*Primary Examiner* — Dennis Heyer
(74) *Attorney, Agent, or Firm* — Birch, Stewart, Kolasch & Birch, LLP

(57) ABSTRACT

The present invention can provide a method having superior safety for protecting field corn from damage by a plant pathogen. The method includes a step of applying mefentrifluconazole to foliage of field corn, seeds of field corn or a soil of the cultivation area of field corn, wherein the application rate of mefentrifluconazole is 20 to 500 g per hectare of cultivation area.

2 Claims, No Drawings

METHOD OF PROTECTING FIELD CORN FROM DAMAGE BY A PLANT PATHOGEN

CROSS-REFERENCE TO RELATED APPLICATION

This application claims priority under 35 U.S.C.§ 119(b) to Japanese Application No. 2019-066003, filed Mar. 29, 2019, the disclosure of which is incorporated herein by reference in its entirety.

TECHNICAL FIELD

The present invention relates to a method of protecting field corn from damage by a plant pathogen.

BACKGROUND ART

Hitherto, a method of applying mefentrifluconazole has been known, as a method for controlling a plant pathogen on corn (see Patent Document 1). Also, various types of corn such as field corn, sweet corn, popcorn, and waxy corn are known (see Non-Patent Documents 1, 2). However, it is not known that field corn, especially, can be safely protected from damage by a plant pathogen by applying mefentrifluconazole at certain application rate.

CITATION LIST

Patent Document

Patent Document 1: WO2013/007767

Non-Patent Document

Non-Patent Document 1: https://www.bestfoodfacts.org/corn/
Non-Patent Document 2: Genetics 99, 275-284.

SUMMARY OF THE INVENTION

Problems to be Solved by the Invention

An object of the present invention is to provide a method having superior safety for protecting field corn from damage by a plant pathogen.

Means for Solving the Problems

The present inventor has found out that field corn can be safely protected from damage by a plant pathogen by applying mefentrifluconazole at certain application rates to foliage of field corn, seeds of field corn, or a soil of cultivation area of field corn.

The present invention includes the following aspects [1] and [2].

[1] A method of protecting field corn from damage by a plant pathogen in a cultivation area of field corn, the method including a step of applying mefentrifluconazole to foliage of field corn, seeds of field corn or a soil of the cultivation area of field corn, wherein the application rate of mefentrifluconazole is 20 to 500 g per hectare of the cultivation area.

[2] The method according to [1], wherein mefentrifluconazole is applied to foliage of field corn.

Effect of the Invention

Field corn can be safely protected from damage by a plant pathogen according to the present invention.

MODE FOR CARRYING OUT THE INVENTION

The method of protecting field corn from damage by a plant pathogen of the present invention (hereinafter, sometimes referred to as "present method") includes a step of applying mefentrifluconazole to foliage of field corn, seeds of field corn or a soil of cultivation area of field corn.

Mefentrifluconazole is a triazole-type sterol biosynthesis inhibitor, and can be manufactured by a known method.

Field corn in the present method is also known as dent corn in general (see Non-Patent Document 1), and is a variety group established from *Zea mays* var. indentata and/or *Zea mays* var. indurata as major ancestors. Examples of corn which does not belong to field corn include popcorn (*Zea mays* var. everta), sweet corn (*Zea mays* var. saccharata), waxy corn (*Zea mays* var. ceratina), pod corn (*Zea mays* var. tunica), and the like.

In the present method, variations within field corn are not particularly limited as long as the field corn is a variety which is usually cultivated. For example, field corn belonging to diverse maturity groups from early-maturing to late-maturing can be used. Also, the varieties are not limited by diverse intended usages of the harvest of field corn. For example, field corn for any of the intended usages such as seed production, ornamentals, green manures, silage, grains, and the like can be used. For grains, field corn for any of the intended usages such as starch, ethanol, oil extraction, feed, sugar production, and the like can be used.

Examples of field corn varieties include Pioneer Dent Series (for example, P2088), Dekalb Corn Series (for example, DKC5632), MAS40F, Koshu, and the like. Although the weight of seeds of field corn which can be used in the present method is not particularly limited, a seed weight of field corn is usually within a range of 100 to 400 mg/seed, more preferably 200 to 300 mg/seed.

The field corn may be the one producible by natural crossing, plants producible by a mutation, F1 hybrid plants, or transgenic plants (also called genetically modified plants). These plants generally have characteristics such as tolerance to herbicides, accumulation of substances harmful to insect pests, reduction in sensitivity to diseases, increase in yield potential, improvement in resistance to biotic or abiotic stress factors, accumulation of substances, and improvement in preservability and processability.

The F1 hybrid plants are those which are each a first filial hybrid obtained by crossing two different varieties with each other and usually have characteristics of heterosis, which is a nature of having more excellent trait than both of the parents. The transgenic plants are those which are obtained by introducing an exogeneous gene from other organisms such as microorganisms and have characteristics like those that cannot be easily obtained by crossbreeding, mutation induction, or natural recombination in natural environments.

Examples of the technologies used to create the above plants include conventional type variety improvement technologies; genetic recombination technologies; genome breeding technologies; new breeding technologies; and genome editing technologies. The conventional type variety improvement technologies are specifically technologies for obtaining plants having desired properties by a mutation and crossing. The genetic recombination technologies are technologies in which a target gene (DNA) is extracted from a certain organism (for example, microorganism) to introduce it into a genome of a different target organism, thereby imparting new properties to the organism, and antisense technologies or RNA interference technologies for imparting new or improved characteristics by silencing a certain genes existing in plants. The genome breeding technologies are those improving breeding efficiency by using genome information and include DNA marker (also called genome markers or genetical markers) breeding technologies and genomic selection. For example, the DNA marker breeding is a method in which a progeny having a target gene with a useful trait is selected from a lot of cross progenies by using a DNA marker which is a DNA sequence and is a marker of the presence position of a gene with a specific useful trait on a genome. This method has the characteristics that the time required for breeding can be efficiently reduced by analyzing the cross progeny using a DNA marker when the progeny is a juvenile plant.

Also, the genomic selection is a technique in which a prediction formula is created from a phenotype obtained in advance and genome information to predict the characteristics from the prediction formula and the genome information without any evaluation of the phenotype and is technologies contributing to improvement in efficient breeding. The new breeding techniques are a generic term of variety-improvement (=breeding) techniques that are combinations of molecular biological techniques. Examples of the new breeding techniques include cisgenesis/intragenesis, introduction of an oligonucleotide-directed mutation, RNA-dependent DNA methylation, grafting onto a GM rootstock or scion, reverse breeding, agroinfiltration, and seed production technology (SPT). The genome editing technologies are those in which genetic information is transformed in a sequence-specific manner which enables, for example, deletion of a base sequence, substitution of an amino acid sequence, and introduction of an exogenous gene. Examples of tools for these techniques include sequence-specific genome modification techniques such as zinc-finger nuclease (ZFN), TALEN, CRISPR/Cas9, CRISPER/Cpfl, and Meganuclease which each enable sequence-specific DNA scission and CAS9 Nickase and Target-AID which are each created by modifying the aforementioned tools.

Examples of the plants mentioned above include plants listed in GM APPROVAL DATABASE of genetically modified crops in the electronic information site (http://www.isaaa.org/) of INTERNATIONAL SERVICE for the ACQUISITION of AGRI-BIOTECH APPLICATIONS (ISAAA). More specifically, these examples include herbicide tolerant plants, insect pest resistant plants, disease resistant plants, and quality modified (for example, increase or decrease in content of a certain component or change in composition) plants of products (for example, starch, amino acid, and fatty acid), fertile trait modified plants, abiotic stress tolerant plants, or plants modified in traits relating to growth and yield.

Examples of plants to which tolerance to herbicides is imparted are given as follows.

The tolerance to herbicides is obtained, for example, by reducing the compatibility of a chemical with its target, by rapid metabolism (for example, breakdown or modification) resulting from the expression of a chemical deactivation enzyme, or by inhibiting the incorporation of a chemical into a plant body or the transfer of the chemical in the plant body.

The plants to which herbicide tolerance is imparted by genetic recombination technologies include plants to which tolerances to the following inhibitors are imparted by genetic recombination technologies: 4-hydroxyphenyl pyruvate dioxygenase (hereinafter abbreviated as HPPD) inhibitors such as isoxaflutole and mesotrione, acetolactate synthetase (hereinafter abbreviated as ALS) inhibitors such as imidazolinone type herbicides including imazethapyr and sulfonylurea type herbicides including thifensulfuron-methyl, 5-enolpyruvylshikimate-3-phosphate synthase (hereinafter abbreviated as EPSP) inhibitors such as glyphosate, glutamine synthetase inhibitors such as glufosinate, auxin type herbicides such as 2,4-D and dicamba, oxynil type herbicides including bromoxynil, and protoporphyrinogen oxidase (herein after abbreviated as PPO) such as flumioxazin.

In the present method, mefentrifluconazole is usually used after making formulation by mixing with a carrier such as a solid or liquid carrier, and adding auxiliary agents for formulation such as a surfactant as necessary. In the case of making formulation, preferable formulation type is a soluble liquid, soluble granule, an aqueous suspension concentrate, oil-based liquid suspension, wettable powder, water dispersible granule, granule, aqueous emulsion, oil-based emulsion, and emulsifiable concentrate. More preferable formulation type is aqueous suspension concentrate. Moreover, a formulation containing mefentrifluconazole singly as an active ingredient may be independently used or may be tank-mixed with a formulation containing other fungicides as active ingredients. Also, a formulation containing mefentrifluconazole and other fungicide may be used. Also, a formulation containing mefentrifluconazole and other fungicide as active ingredients may be tank-mixed with a formulation containing, as active ingredients, fungicide different from the above fungicides. The content of the active ingredients (mefentrifluconazole or a total of mefentrifluconazole and other fungicides) in the formulation is usually within a range of 0.01 to 90% by weight, preferably 1 to 80% by weight.

In the present method, "applying mefentrifluconazole to foliage of field corn" means to apply mefentrifluconazole to foliage of field corn planted in the cultivation area.

In the present method, when applying mefentrifluconazole to foliage of field corn or a soil of the cultivation area of field corn, the application is usually conducted using a spray dilution prepared by mixing a formulation containing mefentrifluconazole with water. These applications may be conducted uniformly on the cultivation area, or may be conducted locally as a spot treatment onto foliage of field corn or the soil around the field corn. The amount of the dilution to be sprayed is usually 10 to 1000 L, preferably 100 to 500 L, and more preferably 140 to 300 L per hectare of cultivation area of field corn though no particular limitation is imposed on it.

In the present method, when applying mefentrifluconazole to seeds of field corn, the treatment is usually conducted by coating or spraying seeds with a dilution prepared by mixing a formulation containing mefentrifluconazole with water.

In the present method, the application rate of mefentrifluconazole is usually within a range of 20 to 500 g, preferably 40 to 200 g, more preferably 60 to 150 g per hectare of cultivation area of field corn. Examples of the specific application rates of mefentrifluconazole include 30 g, 50 g, 70 g, 80 g, 100 g, 120 g, 250 g, 300 g, and 400 g per hectare of cultivation area of field corn. These application rates can be described with "approximately." "Approximately" means plus/minus 10%, so, for example, "approximately 100 g per hectare" means "90 to 110 g per hectare."

In the present method, when applying mefentrifluconazole locally as a spot treatment onto foliage of field corn or the soil around the field corn, usually 0.001 to 2 mg of mefentrifluconazole is applied per field corn plant. Preferably, 0.01 to 1 mg of mefentrifluconazole is applied per field corn plant. For example when 0.5 mg of mefentrifluconazole is applied locally per plant as a spot treatment and 400,000 plants are grown per hectare of cultivation area, the application rate of mefentrifluconazole is 200 g per hectare of cultivation area of field corn.

In the present method, when applying mefentrifluconazole to seeds of field corn, 0.001 to 1 mg of mefentrifluconazole is usually applied per seed of field corn. Preferably 0.01 to 0.2 mg of mefentrifluconazole is applied per seed of field corn. Seeds treated with mefentrifluconazole are usually sown uniformly to cultivation area so that the application rates of mefentrifluconazole per hectare of cultivation area may be a desired range. For example, when 0.1 mg of mefentrifluconazole is applied per seed, and 1,000,000 seeds are sown per hectare of cultivation area, the application rate of mefentrifluconazole is 100 g per hectare of cultivation area.

Although a period of time for conducting the present method is not particularly limited, the period of time is usually within a range from 5 a.m. to 9 p.m., and the photon flux density at land surface of the place where the present method is conducted is usually 10 to 2500 μmol/m²/s.

The spray pressure when conducting the present method is usually 30 to 120 PSI and preferably 40 to 80 PSI though no particular limitation is imposed on it. Here, the spray pressure is a set value just before the dilution is introduced into the nozzle.

The nozzle used in the present method may be flat-fan nozzles or drift-reducing nozzles. Examples of flat-fan nozzles include Teejet110 series and XR Teejet110 series manufactured by Teejet Company. When using these nozzles, the spray pressure is generally 30 to 120 PSI and the volume median diameter of liquid droplets discharged from the nozzle is usually less than 430 micro meter. The drift-reducing nozzle is a nozzle which leads to less drift compared with a flat-fan nozzle and which is called an air induction nozzle or pre-orifice nozzle. The volume median diameter of a liquid droplet discharged from the drift-reducing nozzle is usually 430 micro meter or more.

In the present method, when applying mefentrifluconazole to seeds of field corn, the application is usually conducted before sowing the seeds. In the present method, when applying mefentrifluconazole to foliage of field corn, the application is conducted usually between just after emergence of field corn and its harvesting stage, more preferably between 1 leaf stage of field corn and its grain filling stage, further preferably between 2 leaf stage of field corn and its silking stage.

In the present method, seeds of field corn may be treated with one or more compounds selected from the group consisting of insecticidal compounds, nematicidal compounds, fungicidal compounds except mefentrifluconazole, and plant growth regulators. Examples of compounds to be used for the seed treatment include neonicotinoid compounds, diamide compounds, carbamate compounds, organophosphorous compounds, biological nematicidal compounds, other insecticidal compounds and nematicidal compounds, strobilurin compounds, metalaxyl compounds, SDHI compounds, other fungicidal compounds except mefentrifluconazole, and plant growth regulators.

Plant pathogens in the present method are usually fungi. Examples of Fungi include Ascomycota, Basidiomycota, Blasocladiomycota, Chytridiomycota, Mucoromycota and Olpidiomycota. Examples of specific plant pathogens include the following. The words in parentheses is damage caused by the plant pathogen (plant disease).

*Puccinia sorghi*(corn rust), *Puccinia polysora*(corn Southern rust), *Setosphaeria turcica=Exserohilum turcicum* (Norther corn leaf blight), *Physopella zeae* (corn tropical rust), *Cochliobolus heterostrophus* (=*Bipolaris maydis*: Northern corn leaf spot), *Colletotrichum graminicola* (corn antracnose), *Cercospora zeae-maydis* (corn grey leaf spot), *Kabatiella zeae* (corn eye spot), *Phaeosphaeria maydis* (corn *Phaeosphaeria* leaf spot), *Stenocarpella maydis*+ *Stenocarpella macrospora* (corn *diplodia* ear rot), *Fusarium graminearum*+*Fusarium verticilioides*+*Colletotrichum graminicola* (corn stalk rot), *Ustilago maydis* (corn smut), *Physoderma maydis* (corn *Physoderma* brown spot), *Cochliobolus carbonum* (Northern corn leaf spot), *Phyllosticta maydis* (corn yellow leaf blight).

In the above plant pathogens, variations within the species are not particularly limited. Namely, the pathogens also include any plant pathogens having reduced sensitivity (or resistance) to specific fungicides. The reduced sensitivity may be attributed to a mutation at a target site (target site mutations), or may be attributed to a factor other than target site mutation (non-target site mutations). Target site mutations include amino acid substitutions in target proteins caused by a mutation in the corresponding open reading frame, and over expression of the target proteins caused by deletion of a suppressor sequence or an increase of an enhancer sequence at the promotor region, or amplification of gene copy number. The factors of resistance by non-target site mutations include acceleration of efflux of fungicides coming into cells out of the cells by ABC transporter and MDS transporter and the like. It also includes detoxification of fungicides by metabolism.

Examples of aforementioned specific fungicides include nucleic acid synthesis inhibitors (such as phenylamide fungicides, acylamino acid fungicides, DNA topoisomerase type II fungicides), mitosis and cell division inhibitors (such as MBC fungicides, N-phenylcarbamate fungicides), respiration inhibitors (such as QoI fungicides, QiI fungicides, and SDHI fungicides), amino acid synthesis and protein synthesis inhibitors such as (anilinopyrimidine fungicides), signal transduction inhibitors (such as phenylyprole fungicides, dicarboximide fungicides), lipid synthesis and cell membrane synthesis inhibitors (such as phosphorothiorate fungicides, dithiorane fungicides, aromatic hydrocarbyl fungicides, heteroaromatic fungicides, carmabate fungicides), sterol biosynthesis inhibitors (for example, DMI fungicides such as triazoles, hyroxyanlide fungicides, aminopyrazolinone fungicides), cell wall synthesis inhibitors (such as polyoxin fungicides, Carboxylic acid amide fungicides), melanin synthesis inhibitors (such as MBI-R fungicides, MBI-D fungicides, MBI-P fungicides), and other fungicides (such as cyanoacetamidoxim fungicides, phenylacetamide fungicides).

In the present method, mefentrifluconazole may be used in combination with one or more other fungicides. For here, using in combination includes tank-mix, pre-mix, and sequential treatment. In the case of sequential treatment, the order of the treatment is not particularly limited.

In the present method, fungicide used in combination with mefentrifluconazole is preferably pyraclostrobin, fluoyram or fluxapyroxad.

When aforementioned fungicide is used in combination with mefentrifluconazole, the weight ratio of mefentrifluconazole to other fungicide is usually within a range of 1:0.001 to 1:100, preferably 1:0.01 to 1:10, more preferably 1:0.1 to 1:5. Examples of the specific weight ratios include 1:0.02, 1:0.04, 1:0.06, 1:0.08, 1:0.2, 1:0.4, 1:0.6, 1:0.8, 1:1, 1:1.5, 1:2, 1:2.5, 1:3, and 1:4. These weight ratios may be described with approximately. Approximately means plus/minus 10%, so, for example "approximately 1:2" means 1:1.8 to 1:2.2.

The cultivation of field corn in the present invention can be managed according to the plant-nutrition in the common crop cultivation. The fertilization system may be based on Precision Agriculture adopting variable rate application or may be conventionally uniform one. In addition, nitrogen fixation bacteria and mycorrhizal fungi may be inoculated by seed treatment.

EXAMPLES

The present invention will be explained by way of examples, but the present invention should not be limited thereto.

Example 1

Field corn is sown to a pot filled with a soil. It is incubated for 7 days in a greenhouse. Mefentrifluconazole spray liquid (prepared by diluting an aqueous suspension concentrate of mefentrifluconazole with water) is uniformly sprayed onto the foliage of field corn at the amount of 200 L per hectare so that the application rate of mefentrifluconazole may be 500 g per hectare. On the next day of the spraying, a pathogen of grey leaf spot (*Cercospora zeae-maydis*) is inoculated to the foliage of field corn. The field corn is incubated in a greenhouse for 14 days from the inoculation, and then fresh weight of the aerial part of the field corn is measured. It is confirmed that the fresh weight is equivalent to that of the control where field corn is not treated with mefentrifluconazole and the pathogen is not inoculated (no-treatment-no-inoculation control) and is bigger than that of the control where field corn is not treated with mefentrifluconazole and the pathogen is inoculated (no-treatment-inoculation control).

Comparative Example 1

The same procedure of the example 1 is repeated except for replacing field corn with popcorn, sweet corn, or waxy corn. It is confirmed that the fresh weight of popcorn, sweet corn, or waxy corn is smaller than that of the corresponding no-treatment-no-inoculation control and is equivalent to that of the corresponding no-treatment-inoculation control.

Example 2

Seeds of field corn are coated with a mefentrifluconazole aqueous suspension concentrate so that the amount of mefentrifluconazole to be applied to each seed may be 0.2 mg. Then, the field corn seeds are sown to a pot filled with a soil at a sowing rate of 100,000 seeds per hectare. That is, the application rate of mefentrifluconazole is 20 g per hectare. Then, the field corn is incubated in a greenhouse for 10 days, followed by inoculating a pathogen of grey leaf spot (*Cercospora zeae-maydis*) to the foliage of field corn. The field corn is incubated in a greenhouse for 14 days from the inoculation, and then the fresh weight of the aerial part of the field corn is measured. It is confirmed that the fresh weight is equivalent to that of the control where field corn is not treated with mefentrifluconazole and the pathogen is not inoculated (no-treatment-no-inoculation control) and is bigger than that of the control where field corn is not treated with mefentrifluconazole and the pathogen is inoculated (no-treatment-inoculation control).

Comparative Example 2

The same procedure of the example 2 is repeated except for replacing field corn with popcorn, sweet corn, or waxy corn. It is confirmed that the fresh weight of popcorn, sweet corn, or waxy corn is smaller than that of the corresponding no-treatment-no-inoculation control and is equivalent to that of the corresponding no-treatment-inoculation control.

Example 3

Field corn is sown to a pot filled with a soil at a sowing rate of 1,000,000 seeds per hectare. The field corn is incubated for 10 days in a greenhouse, and then mefentrifluconazole dilution liquid (prepared by diluting an aqueous suspension concentrate of mefentrifluconazole with water) is dripped onto the primary leaf of field corn so that the amount of mefentrifluconazole to be applied to each plant may be 0.2 mg. That is, the application rate of mefentrifluconazole is 200 g per hectare. On the next day of the application, a pathogen of grey leaf spot (*Cercospora zeae-maydis*) is inoculated to the foliage of field corn. The field corn is incubated in a greenhouse for 14 days from the inoculation, and then fresh weight of the aerial part of the field corn is measured. It is confirmed that the fresh weight is equivalent to that of the control where field corn is not treated with mefentrifluconazole and the pathogen is not inoculated (no-treatment-no-inoculation control) and is bigger than that of the control where field corn is not treated with mefentrifluconazole and the pathogen is inoculated (no-treatment-inoculation control).

Comparative Example 3

The same procedure of the example 3 is repeated except for replacing field corn with popcorn, sweet corn, or waxy corn. It is confirmed that the fresh weight of popcorn, sweet corn, or waxy corn is smaller than that of the corresponding no-treatment-no-inoculation control and is equivalent to that of the corresponding no-treatment-inoculation control.

Example 4

Seeds of three varieties of field corn were separately dipped in a mefentrifluconazole dilution liquid (prepared by diluting an aqueous suspension concentrate of mefentrifluconazole with water) so that the amount of mefentrifluconazole to be applied to each seed might be 0.2 mg. Then, the field corn seeds were sown to a pot filled with a soil at a sowing rate of 1,000,000 seeds per hectare. That is, the application rate of mefentrifluconazole was 200 g per hectare. Each field corn was incubated in a greenhouse for 12 days from the sowing, and then a pathogen of grey leaf spot (*Cercospora zeae-maydis*) was inoculated to the foliage of each field corn. Each field corn was incubated in a greenhouse for 7 days from the inoculation, and then plant length of the aerial part of each field corn was measured. The plant length is referred to as 'the plant length in treatment plot'.

As a control experiment, the same procedure was repeated except that dipping treatment with mefentrifluconazole dilution liquid and the inoculation of the pathogen were not conducted. The plant length obtained in the control experiment is referred to as 'the plant length in control plot'.

The results are shown in Table 1.

TABLE 1

| Corn/<br>Variety | Plant length<br>in treatment<br>plot (A) (cm) | Plant length<br>in control<br>plot (B) (cm) | Treatment/<br>control ratio<br>(100 × A/B) |
|---|---|---|---|
| Field corn/<br>DKC5632 | 58 | 61 | 95 |
| Field corn/<br>MAS40F | 61 | 63 | 97 |
| Field corn/<br>Koshu | 63 | 60 | 105 |

Comparative Example 4

The same procedure of the example 4 was repeated except for replacing three varieties of field corn with a variety of popcorn, and two varieties of waxy corn. The results are shown in Table 2. As shown in Tables 1 and 2, field corns were protected much more effectively compared with popcorn or waxy corns.

TABLE 2

| Corn/<br>Variety | Plant length<br>in treatment<br>plot (A) (cm) | Plant length<br>in control<br>plot (B) (cm) | Treatment/<br>control ratio<br>(100 × A/B) |
|---|---|---|---|
| Popcorn/<br>Yuki-pop | 45 | 56 | 80 |
| Waxy corn/<br>Shiro-mochi | 51 | 59 | 86 |
| Waxy corn/<br>Ki-mochi | 30 | 43 | 70 |

Example 5

Four varieties of field corn were sown to a pot filled with a soil at a sowing rate of 1,000,000 seeds per hectare. Then each field corn was incubated for 7 days in a greenhouse. A mefentrifluconazole dilution liquid (prepared by diluting an aqueous suspension concentrate of mefentrifluconazole with water) is dripped onto the first leaf of field corn plants so that the amount of mefentrifluconazole to be applied to each plant might be 0.1 mg. That is, the application rate of mefentrifluconazole was 100 g per hectare. Five days after the application, a pathogen of grey leaf spot (*Cercospora zeae-maydis*) was inoculated to the foliage of each field corn. Each field corn was incubated in a greenhouse for 7 days from the inoculation, and then plant length of the aerial part of each field corn was measured. The plant length is referred to as 'the plant length in treatment plot'.

As a control experiment, the same procedure was repeated except that dripping treatment with mefentrifluconazole dilution liquid and the inoculation of the pathogen were not conducted. The plant length obtained in the control experiment is referred to as 'the plant length in control plot'.

The results are shown in Table 3. As shown in Table 3, each field corn was successfully protected from the damage by the pathogen.

TABLE 3

| Corn/<br>Variety | Plant length<br>in treatment<br>plot (A) (cm) | Plant length<br>in control<br>plot (B) (cm) | Treatment/<br>control ratio<br>(100 × A/B) |
|---|---|---|---|
| Field corn/<br>Pioneer 2088 | 62 | 60 | 103 |
| Field corn/<br>DKC5632 | 63 | 61 | 103 |
| Field corn/<br>MAS40F | 64 | 63 | 102 |
| Field corn/<br>Koshu | 65 | 60 | 108 |

Comparative Example 5

The same procedure of the example 5 was repeated except for replacing four varieties of field corn with two varieties of popcorn, a variety of sweet corn, and two varieties of waxy corn. The results are shown in Table 4. As shown in Table 4, each of popcorns, sweet corn and waxy corns was not successfully protected from the damage by the pathogen.

TABLE 4

| Corn/<br>Variety | Plant length<br>in treatment<br>plot (A) (cm) | Plant length<br>in control<br>plot (B) (cm) | Treatment/<br>control ratio<br>(100 × A/B) |
|---|---|---|---|
| Popcorn/<br>Yuki-pop | 53 | 63 | 84 |
| Popcorn/<br>Maru-pop | 45 | 56 | 80 |
| Sweet corn/<br>Rancher 82 | 31 | 34 | 91 |
| Waxy corn/<br>Shiro-mochi | 43 | 59 | 73 |
| Waxy corn/<br>Ki-mochi | 29 | 43 | 67 |

INDUSTRIAL APPLICABILITY

Field corn can be safely protected from damage by a plant pathogen according to the present invention.

The invention claimed is:

1. A method of protecting field corn from damage by a plant pathogen in a cultivation area of field corn, the method comprising a step of applying mefentrifluconazole to foliage of field corn, seeds of field corn or a soil of the cultivation area of field corn, wherein the application rate of mefentrifluconazole is 20 to 500 g per hectare of the cultivation area.

2. The method according to claim 1, wherein mefentrifluconazole is applied to foliage of field corn.

\* \* \* \* \*